United States Patent
Kaule et al.

(10) Patent No.: US 12,064,064 B2
(45) Date of Patent: Aug. 20, 2024

(54) RETRACTABLE SHOWER DOOR

(71) Applicant: Kohler Co., Kohler, WI (US)

(72) Inventors: Brian M. Kaule, Sheboygan, WI (US); Ken Hanna, Bellingham, WA (US)

(73) Assignee: KOHLER CO., Kohler, WI (US)

( * ) Notice: Subject to any disclaimer, the term of this patent is extended or adjusted under 35 U.S.C. 154(b) by 612 days.

(21) Appl. No.: 17/186,964

(22) Filed: Feb. 26, 2021

(65) Prior Publication Data

US 2021/0267420 A1   Sep. 2, 2021

Related U.S. Application Data

(60) Provisional application No. 62/983,246, filed on Feb. 28, 2020.

(51) Int. Cl.
*E06B 9/60* (2006.01)
*A47K 3/28* (2006.01)
*A47K 3/30* (2006.01)
*A61L 2/10* (2006.01)

(52) U.S. Cl.
CPC .......... *A47K 3/30* (2013.01); *A47K 3/281* (2013.01); *A61L 2/10* (2013.01); *E06B 9/60* (2013.01); *A47K 2201/02* (2013.01); *A61L 2202/11* (2013.01)

(58) Field of Classification Search
None
See application file for complete search history.

(56) References Cited

U.S. PATENT DOCUMENTS

| | | | |
|---|---|---|---|
| 2,756,438 A | | 7/1956 | Soberman |
| 2,840,827 A | | 7/1958 | Calvano |
| 3,050,742 A | * | 8/1962 | Munson ............... A47K 3/38 |
| | | | 4/558 |
| 3,222,689 A | * | 12/1965 | Efron ................ A47K 3/38 |
| | | | 4/608 |
| 3,444,564 A | * | 5/1969 | Lavacchia ........... A47K 3/004 |
| | | | 4/559 |

(Continued)

FOREIGN PATENT DOCUMENTS

| | | |
|---|---|---|
| EP | 0484932 A1 * | 6/1991 |
| EP | 0 958 775 | 11/1999 |

(Continued)

OTHER PUBLICATIONS

International Search Report on PCT PCT/US2021/019952 Dtd May 21, 2021.

(Continued)

*Primary Examiner* — Phi D A
(74) *Attorney, Agent, or Firm* — FOLEY & LARDNER LLP

(57) ABSTRACT

A retractable shower assembly is provided. The retractable door assembly includes a housing, a retractable door, and a spring roller. The housing includes a shelving cavity. The retractable door is operable to move between a retracted position in which the retractable door is retracted into the housing and an extended position in which the retractable door extends out of the housing. The spring roller is configured to bias the retractable door toward the housing when the retractable door is between the retracted position and the extended position.

19 Claims, 5 Drawing Sheets

(56) References Cited

U.S. PATENT DOCUMENTS

| | | | |
|---|---|---|---|
| 3,965,960 A * | 6/1976 | Massey | A47K 3/38 4/558 |
| 4,122,559 A | 10/1978 | Kelly | |
| 4,916,764 A * | 4/1990 | Meaden | A47K 3/38 4/558 |
| 5,033,132 A * | 7/1991 | Greenblatt | A47K 3/38 4/558 |
| 5,231,708 A | 8/1993 | Hansen | |
| 5,332,021 A | 7/1994 | Todd et al. | |
| 5,682,627 A * | 11/1997 | Russell | A47K 3/30 4/558 |
| 5,732,419 A | 3/1998 | Feist | |
| 5,794,281 A | 8/1998 | Shearon | |
| 6,435,254 B1 | 8/2002 | Todd et al. | |
| 6,470,511 B1 | 10/2002 | Smale | |
| 6,655,444 B2 | 12/2003 | Goldenberg et al. | |
| D494,401 S | 8/2004 | Davies et al. | |
| 2006/0191066 A1* | 8/2006 | Johnson | A47K 3/30 4/557 |
| 2006/0230516 A1* | 10/2006 | Wilson | A47K 3/30 4/538 |
| 2015/0327729 A1 | 11/2015 | Tarnowski | |
| 2017/0211325 A1 | 7/2017 | Riemelmoser et al. | |
| 2019/0089550 A1* | 3/2019 | Rexach | E03C 1/057 |
| 2019/0201570 A1* | 7/2019 | Dobrinsky | G01N 21/94 |
| 2022/0000319 A1* | 1/2022 | Rauch | A47K 3/34 |

FOREIGN PATENT DOCUMENTS

| | | | | |
|---|---|---|---|---|
| EP | 1 187 638 | | 12/2000 | |
| EP | 1 366 698 | | 12/2003 | |
| ES | 2153731 | | 3/2001 | |
| FR | 2904523 | | 2/2008 | |
| GB | 2490182 A | * | 10/2012 | A47K 3/281 |
| WO | WO-9749322 A1 | * | 12/1997 | A47K 3/38 |
| WO | WO-2020099894 A1 | * | 5/2020 | A47K 3/30 |

OTHER PUBLICATIONS

International Preliminary Report on Patentability and Written Opinion issued in connection with PCT Appl. Ser. No. PCT/US2021/019952 dated Aug. 30, 2022.

* cited by examiner

RETRACTABLE SHOWER DOOR

CROSS REFERENCE TO RELATED APPLICATIONS

The present application claims priority to U.S. Provisional Patent Application 62/983,246, filed on Feb. 28, 2020, which is hereby incorporated by reference in its entirety.

BACKGROUND

The present application relates generally to shower systems, and more particularly to showers that incorporate a retractable shower door.

SUMMARY

According to an exemplary embodiment, a retractable shower assembly is provided. The retractable door assembly includes a housing, a retractable door, and a spring roller. The housing includes a shelving cavity. The retractable door is operable to move between a retracted position in which the retractable door is retracted into the housing and an extended position in which the retractable door extends out of the housing. The spring roller is configured to bias the retractable door toward the housing when the retractable door is between the retracted position and the extended position.

According to another exemplary embodiment, a retractable shower door assembly is provided. The retractable shower door assembly includes a housing, a spring roller, and a retractable door. The housing includes a shelving cavity extending into the housing and configured to removably receive a shelf within the shelving cavity. The spring roller is positioned within the housing and extends along a length of the housing. The retractable door is operably coupled to the spring roller and operable between a fully extended position and a retracted position. The retractable door includes a first door end coupled to the spring roller and a second door end extendable away from the housing and extendable away from the spring roller. The spring roller applies a unidirectional force to the retractable door to facilitate retraction of the retractable door into the housing.

According to another exemplary embodiment, a retractable shower door assembly is provided. The retractable shower door assembly includes a housing, a spring roller, and a retractable door. The housing includes a first housing end and a second housing end. The housing further includes a cavity between the first housing end and the second housing end. A door slot extends into the housing and is in fluid communication with the cavity. The door slot extends between the first housing end and the second housing end. The spring roller is positioned within the cavity between the first housing end and the second housing end. The retractable door is operably coupled to the spring roller and is positionable between a fully extended position and a retracted positon.

BRIEF DESCRIPTION OF THE DRAWINGS

The details of one or more implementations are set forth in the accompanying drawings and the description below. Other features, aspects, and advantages of the disclosure will become apparent from the description, the drawings, and the claims, in which:

It will be recognized that some or all of the Figures are schematic representations for purposes of illustration. The Figures are provided for the purpose of illustrating one or more implementations with the explicit understanding that they will not be used to limit the scope or the meaning of the claims.

DETAILED DESCRIPTION

Following below are more detailed descriptions of various concepts related to, and implementations of, methods, apparatuses, and systems for showers having a retractable shower door. The various concepts introduced above and discussed in greater detail below may be implemented in any of a number of ways, as the described concepts are not limited to any particular manner of implementation. Examples of specific implementations and applications are provided primarily for illustrative purposes.

Figure 1:
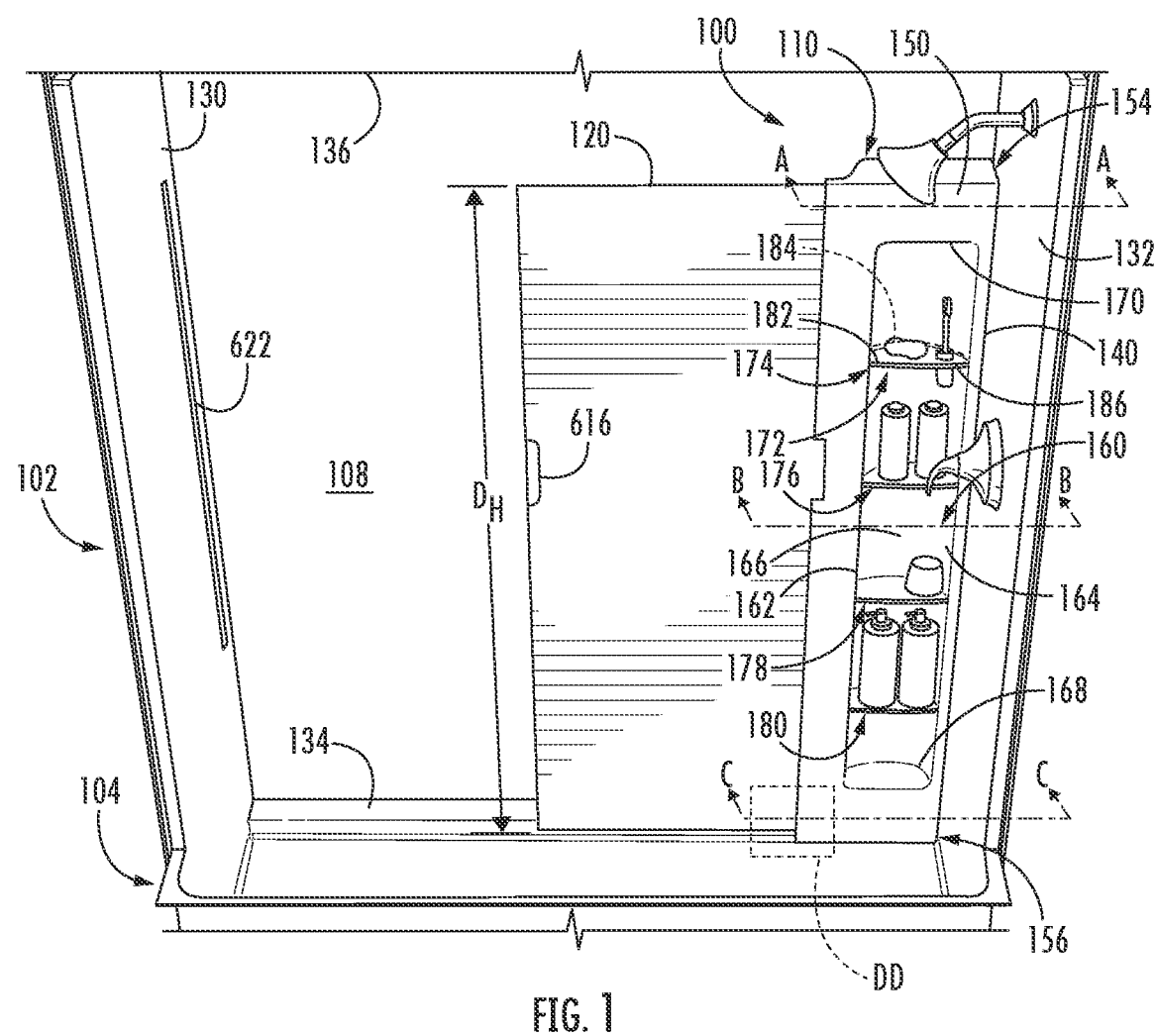
FIG. 1 is a rear perspective view of a retractable shower door assembly installed in a shower environment according to an example embodiment.

FIGS. 1-7 depict an example retractable shower door assembly 100 (e.g., retractable shower curtain system, retractable curtain system, retractable shower door assembly, etc.). Referring specifically to FIG. 1, the retractable shower door assembly 100 may be used in a shower environment 102 including a wash tub (e.g., bath tub, apron front tub, etc.) or a shower receptacle 104 (e.g., shower pan, etc.). Further, the retractable shower door assembly 100 may be configured to extend across a shower environment opening 108 (e.g., shower opening, etc.) of varying widths and heights. In some embodiments, the retractable shower door assembly 100 may be configured to cover either the entirety of the shower environment opening 108 or only a portion of the shower environment opening 108. The retractable shower door assembly 100 may also include shelves, hooks, and similar attachments that may avoid the need for additional peripheral attachments to be used within the shower environment 102.

The retractable shower door assembly 100 includes a housing 110 (e.g., casing, container, enclosure, etc.) and a retractable door 120 (e.g., retractable curtain, shower curtain, etc.). The retractable door 120 is operable between a retracted position (e.g., first position, first door position) and an extended position (e.g., fully extended position. second position, second door position). In the retracted position, the retractable door 120 is retracted into (e.g., received by) the housing 110. The retracted position is binary, meaning that the retractable door 120 is either in the retracted position or is not in the retracted position. In the extended position, the retractable door 120 extends across the shower environment opening 108 and is removably coupled (e.g., releasably coupled, selectively coupled, etc.) proximate to a wall of the shower environment 102 opposite the housing 110, shown as a first wall 130. The retractable door 120 is operable in both a fully extended position and a plurality of partially extended positions. For example, the retractable door 120 may be partially extended to cover a portion of the shower environment opening 108 such that a gap exists between the retractable door 120 and the first wall 130. In other words, the retractable door 120 may be positioned between the retracted position and the extended position.

The shower environment opening 108 includes the first wall 130, a second wall 132, a bottom wall 134, and a ceiling 136 (e.g., top wall). Generally speaking, the shower environment opening 108 is proximate to the front or entry point of the shower environment 102. The first wall 130, the second wall 132, the bottom wall 134, and the ceiling 136 (e.g., ceiling) collectively define a shower environment opening plane, where it is understood that the plane separates "in the shower environment 102" from "out of the shower environment 102." For example, a user of the shower environment 102 may reach into the shower environment (e.g., break the shower environment opening plane) to operate the retractable shower door assembly 100 while standing outside of the shower environment 102. As another example, a user may be inside the shower environment 102 and stay in the shower environment 102 (e.g., not break the shower environment opening plane) to operate the retractable shower door assembly 100. In short, the retractable shower door assembly 100 may be operated from both in and out of the shower environment 102.

Figure 2:
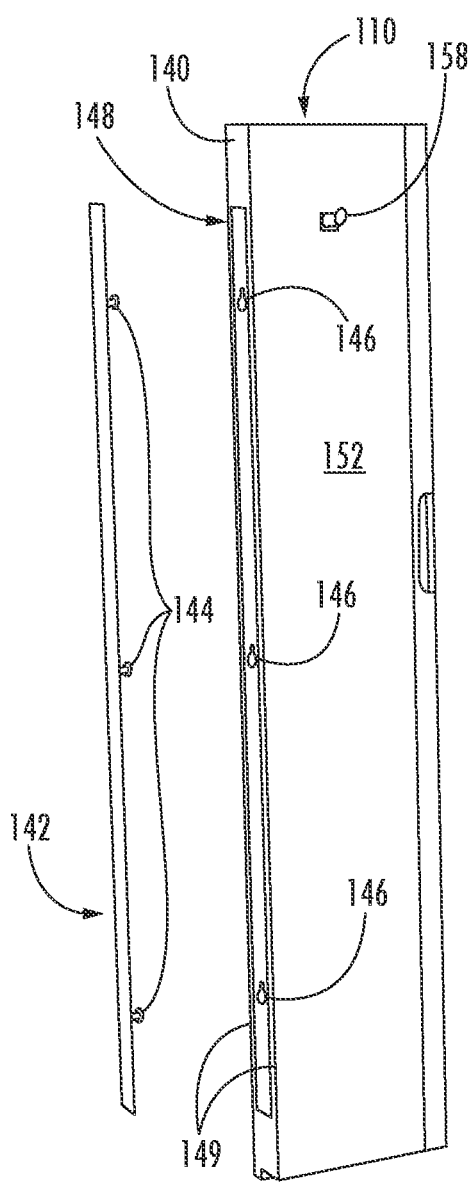
FIG. 2 is a front and exploded view of a portion of the retractable shower door assembly of FIG. 1.

As shown in FIG. 1, the housing 110 is coupled to (e.g., mounted to, fastened to, etc.) the second wall 132. More specifically, as shown in FIG. 2, the housing 110 includes a mounting surface 140 configured to be coupled to the second wall 132. In some embodiments, the mounting surface 140 is generally planar and is fastened to the second wall 132 using an adhesive or fasteners. In some embodiments, the housing 110, and thus the mounting surface 140, is coupled to the second wall 132 using a mounting body 142. The mounting body 142 may be a mounting bar, a mounting bracket, or a similar mounting body.

Figure 3:
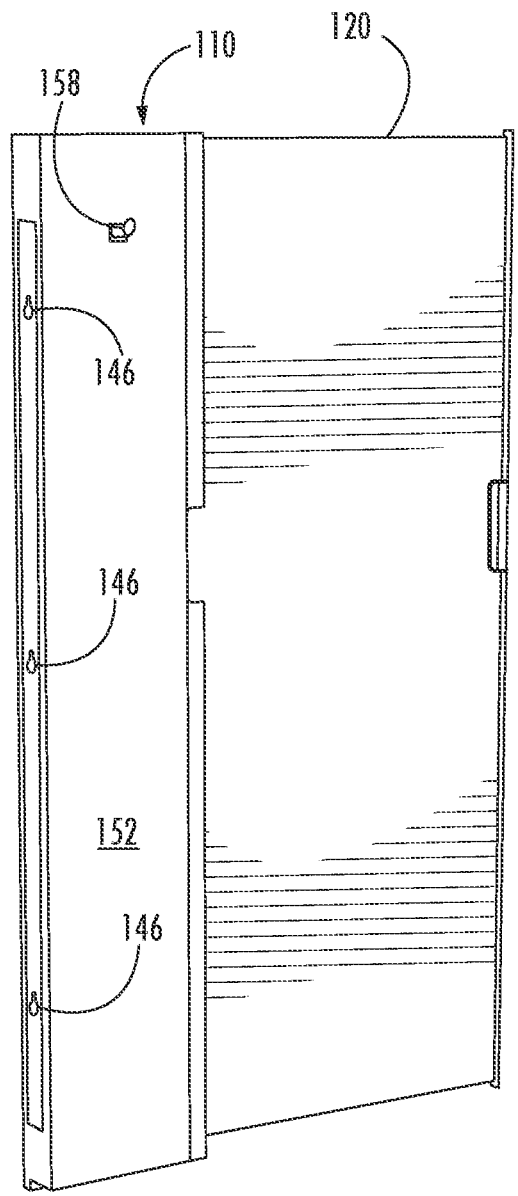
FIG. 3 is a perspective view of a portion of the retractable shower door assembly of FIG. 1.

The mounting body 142 may be permanently coupled to the second wall 132 such as by an adhesive, fasteners, or a combination thereof (e.g., fastened to the second wall 132 and sealed around the edges using a silicon-based caulking). The mounting body 142 may include a projection, shown as a mounting projection 144. The mounting projection 144 may be aligned with a corresponding mounting slot 146 (e.g., keyhole slot, Rockler keyhole slot, etc.). The mounting projection 144 and the mounting slot 146 may cooperate such that the housing 110 is removably coupled to the second wall 132. In some embodiments, the mounting projection 144 is a dome-capped projection configured to extend into the mounting slot 146 at the base of the keyhole slot and then slide upward into the slot of the keyhole slot. The dome interfaces with an inner surface of the housing 110 to prevent movement of the housing 110 away from the mounting body 142. By using a keyhole slot, the housing 110 may be removed from the second wall 132 to be replaced, cleaned, repaired, and otherwise maintained. In some embodiments, the mounting body 142 includes a plurality of mounting projections (e.g., three mounting projections 144) that correspond to a plurality of mounting slots (e.g., three mounting slots 146) in the mounting surface 140 of the housing 110. In some embodiments, the mounting surface 140 includes a mounting cavity 148 (e.g., mounting surface depression) configured to accept the mounting body 142 such that a portion of the mounting surface 140 (e.g., side edges 149 of the mounting surface 140) sits flush against (e.g., may interface with) the second wall 132, hiding the mounting body 142 from view from both inside and outside of the shower environment 102. Referring now to FIG. 3, the retractable door 120 is shown in a partially extended position.

While the housing 110, as outlined above, may be removably coupled to the second wall 132, in some embodiments, the housing 110 is instead removably coupled to the first wall 130. In some embodiments, the mounting slot 146 may be flipped upside-down (e.g., rotated 180-degrees due to the nature of keyhole slots) such that the housing 110 may be properly oriented against the first wall 130. In some embodiments, the mounting slot 146 may be a double-sided keyhole slot (e.g., similar to the Greek letter phi Ø) such that the housing 110 may be removably coupled to either the first wall 130 or the second wall 132 based on the preference of the user. In some embodiments, a retractable shower door assembly 100 may be mounted to both the first wall 130 and the second wall 132, and the respective retractable doors 120 may meet and close in the middle.

In addition to the mounting surface 140, the housing 110 further defines a rearward surface 150 facing generally into the shower environment 102 and a forward surface 152 facing generally out of the shower environment 102. Each of the rearward surface 150 and the forward surface 152 are contiguous with the mounting surface 140. The housing 110 further defines a first (e.g., upper) housing end 154 and a second (e.g., lower) housing end 156. A distance between the first housing end 154 and the second housing end 156 is shown as a housing height DH. The housing height DH may be configured such that the retractable shower door assembly 100 may be used in shower environments using either the shower receptacle 104 or a bathtub. For example, is a user desires to use the retractable shower door assembly 100 in conjunction with the shower receptacle 104, the user may select the retractable shower door assembly 100 having a housing height DH of approximately 60 inches. Thus, there may remain a gap between the ceiling 136 and the first housing end 154. In some embodiments, the user may desire to use the retractable shower door assembly 100 in conjunction with a shower environment having a bathtub. Thus, the user may select a retractable shower door assembly having a housing height DH of approximately 42 inches such that there is a desirable gap between the first housing end 154 and the ceiling 136. In some embodiments, the retractable shower door assembly 100 may be chosen having a housing height DH such that no gap exists between the first housing end 154 and the ceiling 136 (e.g., the housing 110 interfaces with the ceiling 136).

The housing 110 may further include, proximate to the first housing end 154, a projection, shown as a hook 158. The hook 158 may be coupled to the forward surface 152 and extend in a direction generally away from the forward surface 152 (e.g., away from the shower environment 102). The hook 158 may be used to support a towel, a bath robe, a purse, or similar items.

Integrally formed with the housing 110 may be a cavity (e.g., impression, dent, chamber, depression, etc.), shown as a shelving cavity 160. The shelving cavity 160 may extend into the housing 110 in a direction generally away from the rearward surface 150 and toward the forward surface 152, decreasing an internal volume of the housing 110. The shelving cavity 160 is defined by a first cavity wall 162, a second cavity wall 164, a back cavity wall 166, a cavity bottom 168, and a cavity top 170. The shelving cavity 160 may be centrally positioned within the rearward surface 150 such that the shelving cavity 160 is equally spaced from both the first housing end 154 and the second housing end 156. In some embodiments, the shelving cavity 160 is positioned approximately 6-12 inches from each of the first housing end 154 and the second housing end 156.

The cavity bottom 168 may be angled down in a direction generally toward the shower receptacle 104. For example, if water enters the shelving cavity 160, the cavity bottom 168 is structured such that water that hits the cavity bottom 168 is directed away from the housing 110 and out of the shelving cavity 160. This may be desirable in some embodiments to prevent pooling of water in the shelving cavity 160 and to facilitate cleaning of the shelving cavity 160. The cavity top 170 may mirror the cavity bottom 168, the cavity top 170 slanting down and inward (e.g., diagonally away from the first housing end 154 and the rearward surface 150) to facilitate water flow, avoid sharp corners where water may collect, and facilitate cleaning.

Positioned within the shelving cavity 160 may be a shelf 172 (e.g., a first shelf, a support surface, etc.). As shown in FIG. 1, the shelving cavity 160 may include a plurality of shelves, shown as a first shelf 174, a second shelf 176, a third shelf 178, and a fourth shelf 180. The shelf 172 may be removably coupled or removably positioned within the shelving cavity 160, such as through the use of pegs removably inserted into the shelving cavity 160 that support an underside of the shelf 172. In some embodiments, slides are integrally formed with the housing 110 and extend into the shelving cavity 160. The slides are configured to support the shelf 172 and allow the shelf 172 to be removably coupled within the shelving cavity 160 without the need for fasteners and/or adhesives. The slides may be vacuum molded with the housing 110.

The shelf 172 includes a front shelf surface 182 exposed to the shower environment 102 and a rear shelf surface 184, shown by dotted lines. The front shelf surface 182 may be generally planar such that the shelf 172 does not extend outside of the shelving cavity 160 and beyond the rearward surface 150. In some embodiments, the front shelf surface 182 exhibits a slight curvature that matches a slight curvature of the rearward surface 150. In some embodiments, the shelf 172 includes a lip 186 extending upward (e.g., toward the first housing end 154) from the front shelf surface 182, the lip 186 configured to prevent items placed on the shelf 172 from sliding forward and off the shelf 172 and onto the shower receptacle 104. The rear shelf surface 184 may be contoured (e.g., shaped) to sit flush against the shelving cavity 160 (e.g., the entirety of the rear shelf surface 184 may interface with the first cavity wall 162, the second cavity wall 164, and the back cavity wall 166). The matching of the rear shelf surface 184 to the shelving cavity 160 prevents objects from falling between the shelf 172 and the shelving cavity 160. In some embodiments, a plurality of apertures are profiled along the rear shelf surface 184 to facilitate the drainage of water than may enter the shelving cavity 160.

The shelf 172 may be formed of plastic, stainless steel, a polymer, or other non-corrosive materials. In some embodiments, the shelf 172 and the housing 110 are formed from the same material. In some embodiments, the shelf 172 is integrally formed with the housing 110. The shelf 172 may be removed from the shelving cavity 160 such that the shelf 172 may be cleaned or replaced. In some embodiments, the lip 186 may be formed of a different material from the shelf 172. In some embodiments, the lip 186 is selectively coupled to the front shelf surface 182 using latches, fasteners, or an adhesive.

Figure 4:
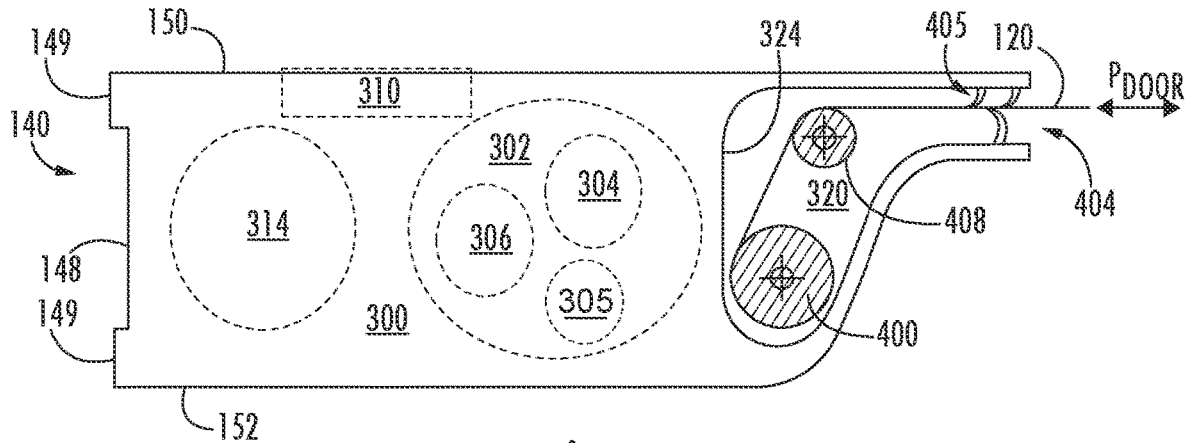
FIG. 4 is a cross-sectional view of a portion of the retractable shower door assembly of FIG. 1 taken along plane A-A.

Referring to FIG. 4, a cross-sectional view of the housing 110 is shown from the top looking down, taken at the line A (shown in FIG. 1). The cross-sectional view is taken between the first housing end 154 and the cavity top 170. Between the first housing end 154 and the cavity top 170 is a first (e.g., top) cavity 300. The first cavity 300 is defined by the forward surface 152, the rearward surface 150, and the mounting surface 140. Positioned within (e.g., built into, etc.) the first cavity 300 may be a door cleaning assembly 302. The door cleaning assembly 302 is configured to clean the retractable door 120 when the retractable door 120 is in the retracted position. In some embodiments, the door cleaning assembly 302 is configured to clean the retractable door 120 as the retractable door 120 transitions into or out of the retracted position.

According to an exemplary embodiment, the door cleaning assembly 302 may be configured to contain a cleanser (e.g., a cleaning substance or solution, such as a cleaning liquid, cleaning fluid, a powdered cleaning concentrate, a liquid cleaning concentrate, or similar cleaning substances and solvents). The door cleaning assembly 302 is configured to discharge some of the cleanser onto the retractable door 120 using a spray nozzle, a pneumatic pump, or a similar cleaning substance discharging device. According to an exemplary embodiment, the cleanser may be configured to be discharged as the retractable door moves between the extended and retracted positions (e.g., as the door retracts toward the retracted position and/or as the door is extended toward the extended position). The discharge of the cleanser may occur automatically or may be performed manually.

In some embodiments, the door cleaning assembly 302 includes an ultraviolet light source 305 in addition to or instead of a system to discharge a cleanser, where the ultraviolet light source 305 is configured to direct ultraviolet light toward one or more surfaces of the retractable door 120 to clean and/or disinfect the door. According to an exemplary embodiment, the ultraviolet light source 305 may be configured to power on when a sensor detects that the retractable door 120 is moving. For example, the ultraviolet light may be configured to turn on when the retractable door begins to move from the retracted to the extended position, or from the extended to the retracted position, or when the retractable door begins to move in either direction. In such a case, the ultraviolet light may be powered off when movement of the retractable door stops or when it reaches the fully retracted or fully extended position. In some embodiments, the ultraviolet light source 305 is always on or may be switched between an on and off state manually by a user.

The door cleaning assembly 302 may be configured to clean the retractable door 120 automatically. For example, the door cleaning assembly 302 may discharge the cleaning substance in response to sensing that the retractable door 120 is transitioning from the extended position to the retracted position (e.g., is retracting). In some embodiments, the door cleaning assembly 302 is configured to clean the retractable door 120 while the retractable door 120 is still wet from use. In some embodiments, the door cleaning assembly 302 cleans the retractable door 120 after the retractable door 120 has dried (e.g., after a set period of time, after dried by a fan, after allowed to air dry, etc.). In some embodiments, the door cleaning assembly 302 operates irrespective of the position of the retractable door 120. For example, the door cleaning assembly 302 may operate based on a timer such that the door cleaning assembly 302 releases a pre-determined about of cleaning substance at predetermined time intervals.

The door cleaning assembly 302 may include a power supply 304, such as batteries, that may be exchanged through a removable panel within the housing, or by removing the door cleaning assembly 302 from the housing 110. The door cleaning assembly 302 may be automatically activated by sensors, such as a proximity sensor 306 that senses when the retractable door 120 is moving (e.g., transitioning between the retracted position and the extended position). In some embodiments, the door cleaning assembly 302 is operated manually, such as by pressing a priming bulb (e.g., as used on lawn mowers) that releases the cleaning substance onto the retractable door 120.

Proximate to the first housing end 154, the housing 110 may include a vent 310 or air holes that allow air to circulate throughout the volume defined by the housing 110. In some embodiments, the housing 110 further includes a fan 314 positioned within the first cavity 300 and in fluid communication with the vent 310 to facilitate the circulation of air throughout the housing 110.

The housing 110 further defines a second cavity 320 that extends between the first housing end 154 and the second housing end 156 and is positioned within the housing 110. Separating the first cavity 300 from the second cavity 320 may be a portion of the housing 110 shown as a sectioning wall 324. The sectioning wall 324 may define a portion of the second cavity 320. In some embodiments, the sectioning wall 324 includes gaps, spaces, holes, and similar features such that the first cavity 300 is in fluid communication with the second cavity 320. For example, fluid communication between the first cavity 300 and the second cavity 320 may allow the vent 310 and the fan 314 to facilitate a circulation of air through the second cavity 320 as well and throughout the first cavity 300 at the same time.

FIG. 4 is similar to a cross-sectional view of the housing 110, from the top looking down, taken at the line C (shown in FIG. 1). Between the second housing end 156 and the cavity bottom 168 is a third (e.g., bottom) cavity (not shown). The third cavity is similar to the first cavity 300. A difference between the third cavity and the first cavity 300 is that the third cavity is positioned proximate to the shower pan 104. However, the third cavity, and more specifically the portions of the housing 110 that define the third cavity, may include a vent, a drain, a fan, and similar features that facilitate the circulation of air throughout the third cavity. In some embodiments, the third cavity is in fluid communication with the second cavity 320.

Figure 5:
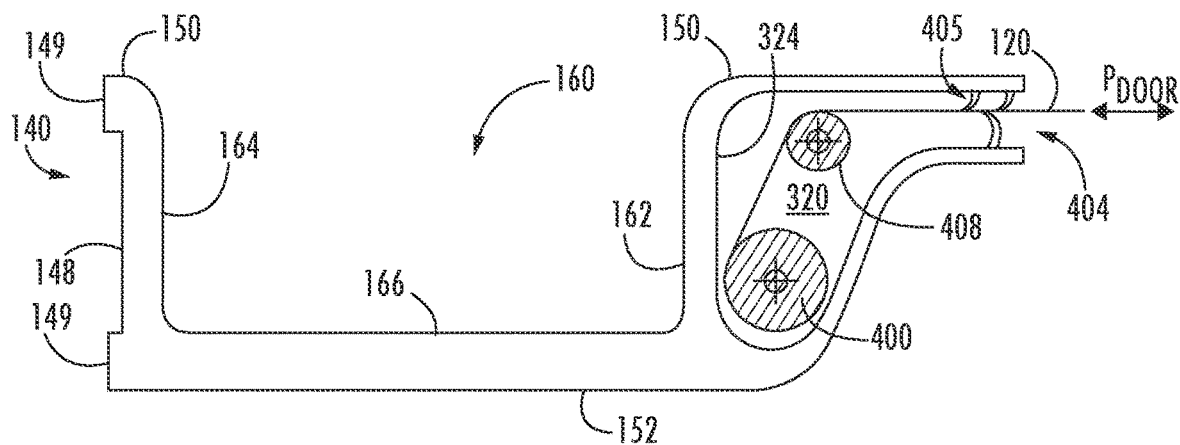
FIG. 5 is a cross-sectional view of a portion of the retractable shower door assembly of FIG. 1 taken along plane B-B.

Turning now to FIG. 5, a cross-sectional view of the retractable shower door assembly 100 is shown about the line B (shown in FIG. 1). The shelving cavity 160 is shown as extending into the rearward surface 150 in a direction generally toward the forward surface 152.

Positioned within the second cavity 320 and extending between the first housing end 154 and the second housing end 156 is the retractable door 120. The retractable door 120 may be formed of a flexible and water resistant material. When the retractable door 120 is in the retracted position, the retractable door 120 is circumferentially wrapped around a cylindrical spring assembly, shown as a spring roller 400. The spring roller 400 may be similar to the spring rollers used on cordless spring roller shades or pull-down projector screens. In some embodiments, the circumference of the spring roller 400 is much smaller than the length of the retractable door 120, and thus the retractable door 120 may be wrapped around the spring roller 400 multiple times when the retractable door 120 is in the retracted position. In some embodiments, the spring roller 400 includes a sensor configured to detect that the spring roller 400 is rotating, thus activating (e.g., actuating, triggering) the door cleaning assembly 302 to provide a cleaning solution (e.g., soap, cleanser, etc.) and/or ultraviolet light to the retractable door 120 as the retractable door 120 transitions from the extended position to the retracted position. For example, the spring roller 400 may be configured to activate (e.g., squeeze a trigger of) the door cleaning assembly 302, but only as the spring roller 400 rotates to transition the retractable door 120 from the extended position to the retracted position.

As shown in FIGS. 4 and 5, the retractable door 120 extends out of the housing 110 (e.g., the second cavity 320) proximate to a slot opposite the mounting surface 140, shown as a door slot 404. The door slot 404 defines a height approximately equal to the housing height DH, and, in some embodiments, defining a height slightly greater than a height of the retractable door 120. In some embodiments, the door slot 404 extends slightly above and slightly below the retractable door 120 to avoid contact with the retractable door 120. In some embodiments, positioned within the housing 110 may be an idler (e.g., idling) roller, shown as a roller 408. The roller 408 may be approximately equal in diameter to the spring roller 400. In some embodiments, the roller 408 defines a smaller diameter than the spring roller 400 to save space within the housing 110 (e.g., the second cavity 320). In some embodiments, the retractable door 120 defines a path between the spring roller 400 and the door slot 404 such that when the retractable door 120 transitions between the retracted position and the extended position, the retractable door 120 interfaces with the walls defining the second cavity 320 (e.g., may interface with the sectioning wall 324). In some embodiments, the spring roller 400 is positioned such that the retractable door 120 does not interface with the housing 110 as the retractable door 120 transitions between the retracted position and the extended position. In some embodiments, the path defined by the retractable door 120 transverses around and interfaces with the roller 408. For example, there may not be room within the housing 110 to position the spring roller 400 such that the retractable door 120 can transition between the retracted position and the extended position without interfacing with the housing 110. The roller 408 may be positioned within the housing 110 such that the retractable door 120 bends at an angle and avoids interfacing with the housing 110 when the retractable curtain transitions between the retracted position and the extended position.

In some embodiments, the door slot 404 includes wipers 405 that interface with the retractable door 120 as the retractable door 120 transitions between the retracted position and the extended position. After a shower, the retractable door 120 may be covered in droplets of water. As the retractable door 120 is transitioned from the extended position to the retracted position (e.g., transitioned toward the retracted position), the wipers 405, which may extend the entire length of the door slot 404, may wipe (e.g., squeegee) the water off of the retractable door 120 such that the water falls onto the shower receptacle 104 instead of sitting between the layers of the retractable door 120 when the retractable door 120 is rolled around the spring roller 400 in the retracted position.

The spring roller 400 includes a tensioned spring system that exerts a force on the retractable door 120. In some embodiments, the spring roller 400 includes an auto-lock feature that is configured to selectively prevent the retraction of the retractable door 120. The auto-lock feature is configured to prevent the spring roller 400 from recoiling when the retractable door 120 is in a partially extended position (e.g., between the retracted position and the extended position) and released. The auto-lock feature locks the spring roller 400 and permits the retractable door 120 to be maintained in a partially extended position without the application of a secondary external force on the retractable door 120. For example, if the retractable door 120 is in the retracted position and then pulled toward the first wall 130 such that a gap exists between the retractable door 120 and the first wall 130, the retractable door 120 will not be retracted into the housing 110 by the spring roller 400 when the retractable door 120 is released. In other words, the spring roller 400 will lock and will not apply a force on the retractable door 120. To re-engage the spring roller 400 and release the auto-lock feature, a slight force may be applied to the retractable door 120 in the direction of the first wall 130. Upon release of the auto-lock feature, the spring roller 400 will again facilitate retraction of the retractable door 120 (e.g., the spring roller 400 will apply a force on the retractable door 120 in a direction generally toward the housing 110).

In some embodiments, the spring roller 400 does not include the auto-lock feature. For example, if the retractable door 120 is in the retracted position and then pulled toward the first wall 130 such that a gap exists between the retractable door 120 and the first wall 130, the retractable door 120 will be retracted into the housing 110 by the spring roller 400 when the retractable door 120 is released. In other words, unless the retractable door 120 is in the extended position, the spring roller 400 will retract the retractable door 120 into the housing 110 until the retractable door 120 in in the retracted position.

Figure 6:
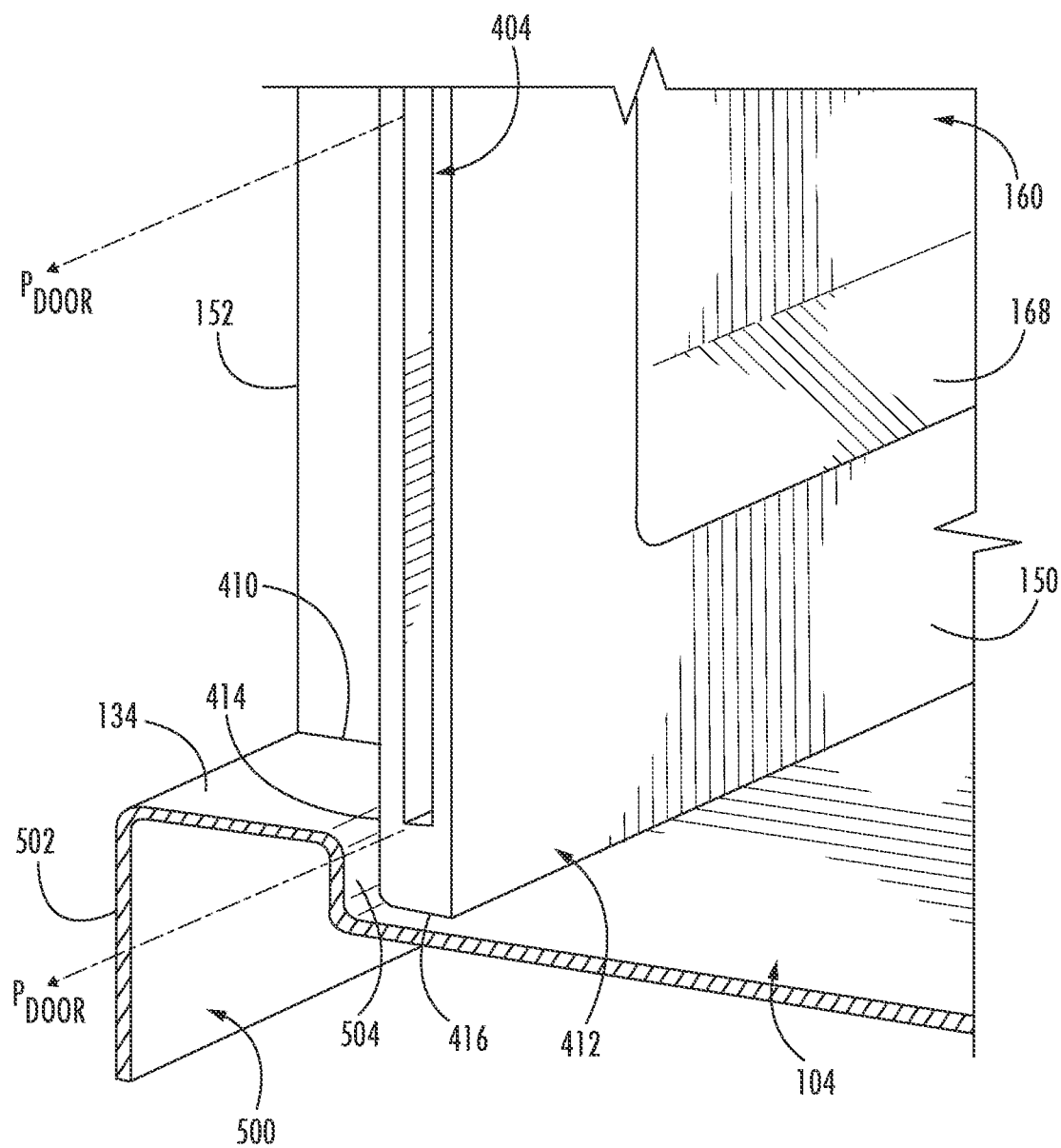
FIG. 6 is a zoomed-in perspective view of a portion of the retractable shower door assembly of FIG. 1 installed in a shower environment, shown through view window DD of FIG. 1.

Turning now to FIG. 6, a zoomed-in perspective view of a portion of the housing 110 through view window DD of FIG. 1 is shown. The housing 110 is shown installed in the shower environment 102 having the shower receptacle 104. The bottom wall 134 of the shower environment 102 is a portion of the shower receptacle 104, shown as a shower step 500. The shower step 500 includes the bottom wall 134, a front step surface 502, and a rear step surface 504. The front step surface 502 is contiguous with the bottom wall 134 and coplanar with the shower environment opening plane. The rear step surface 504 in contiguous with the bottom wall 134 and faces in a direction away from the shower step 500. As shown in FIG. 6, the shower step 500 is a portion of the shower receptacle 104. However, in some embodiments, the shower step 500 may be a portion of a bath tub. For example, a bath tub may include a front apron portion that faces generally away from the shower environment 102 and is in line with the shower environments opening plane. The front apron portion of a bath tub may be taller than the shower step 500 shown in FIG. 6, but the retractable shower door assembly 100 works similarly for either embodiment.

Speaking generally, the housing 110 is structured to position the retractable door 120, and thus the door slot 404, behind the shower step 500 (e.g., along a door plane $P_{door}$) such that when water drains down the retractable door 120, the water flows down the retractable door 120 and lands within the shower receptacle 104. For example, when the retractable door 120 is in the extended position, water that interfaces with the retractable door 120 may flow down the retractable door 120 and into the shower receptacle 104, cooperating with the housing 110 and the shower step 500 to maintain a dry environment (e.g., a dry bathroom floor) outside of the shower environment 102. In some embodiments, the retractable door 120 interfaces with the shower step 500 to prevent water from exiting the shower environment 102 proximate to the shower step 500. In some embodiments, to facilitate the flow of water off of the retractable door 120 and into the shower receptacle 104, the retractable door 120 may include an end cap (e.g., flexible end cap, rubber bumper, etc.) proximate to a bottom of the retractable door 120 that takes advantage of the capillary effect of water to better control the flow of water off of the retractable door 120.

Proximate to the second housing end 156, the housing 110 defines a bottom housing surface 410 configured to interface with the shower step 500 when the retractable shower door assembly 100 is installed in the shower environment 102. More specifically, the bottom wall 134 and the bottom housing surface 410 are configured to interface when the housing 110 is mounted to either of the first wall 130 or the second wall 132.

The housing 110 also includes, proximate to and extending away from the second housing end 156, a flange, shown as a lower flange 412. The lower flange 412 extends away from the bottom housing surface 410 and extends below the bottom wall 134. The lower flange 412 may be positioned behind the shower step 500 such that when water (e.g., from a shower head) interfaces with the rearward surface 150 and the shelving cavity 160, the water will flow (e.g., drip, etc.) down the housing 110, eventually flowing across the lower flange 412 and into the shower receptacle 104. In some embodiments, the lower flange 412 extends perpendicularly from the bottom housing surface 410. The lower flange 412 includes a first flange surface 414 generally perpendicular to and contiguous with the bottom housing surface 410, a second flange surface 416 contiguous with the first flange surface 414, and the rearward surface 150 generally parallel to the first flange surface 414.

In some embodiments, the lower flange 412 is configured to interface with the shower step 500 to facilitate alignment of the housing 110 within the shower environment 102. More specifically, the first flange surface 414 may be configured to interface with the rear step surface 504 when the housing 110 is mounted to either of the first wall 130 or the second wall 132. In some embodiments, the housing 110 is mounted within the shower environment 102 such that no portion of the housing 110 interfaces with the shower step 500. In some embodiments, only the bottom housing surface 410 interfaces with the shower step 500. In some embodiments, the second flange surface 416 does not interface with the shower receptacle 104. For example, the housing 110 may be positioned such that air may circulate between the housing 110 and the shower step 500.

The lower flange 412 is positioned below the door slot 404 to facilitate positioning of the retractable door 120 within the shower environment 102 behind the shower step 500. More specifically, the lower flange 412 and the door slot 404 may be aligned with each other in the same plane, shown as the door plane $P_{door}$, such that as the retractable door 120 transitions between the first positon and the extended position, the retractable door 120 extends away from the door slot 404 along the door plane $P_{door}$, the door plane $P_{door}$ being behind the shower step 500 (where "in front of" the shower step 500 is outside of the shower environment 102 as defined by the shower environment opening plane). As shown in FIG. 6, the retractable door 120 is positioned along the door plane $P_{door}$.

Figure 7:
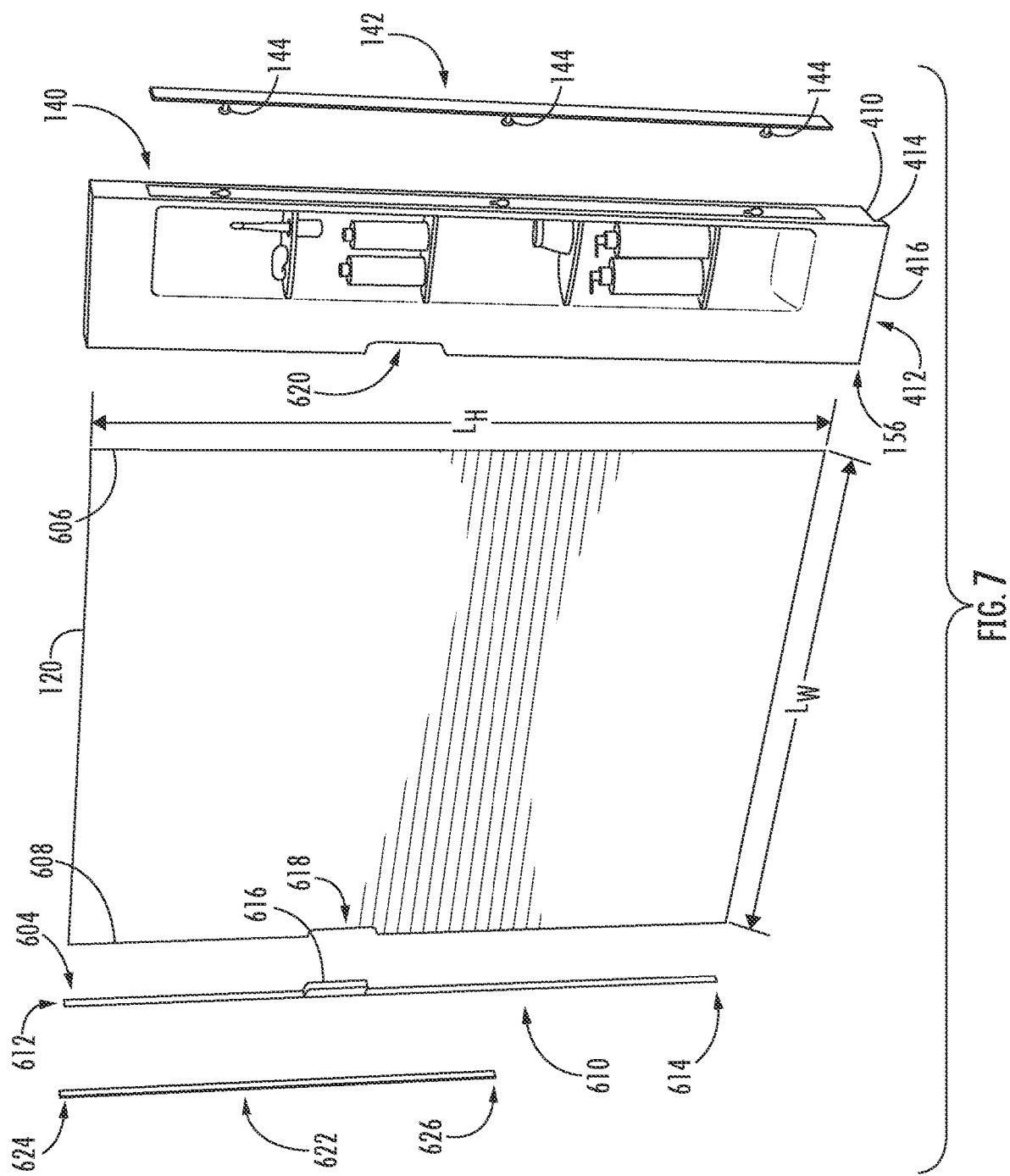
FIG. 7 is an exploded view of the retractable shower door assembly of FIG. 1.

Turning now to FIG. 7, an exploded view of the retractable door 120 is shown. The retractable door 120 defines a door width $L_W$ and a door height $L_H$. The door width $L_W$ may be adequate to extend across a width of the shower environment opening 108. The door height $L_H$ may be approximately equal to a height of the shower environment opening 108. In some embodiments, a gap may exist between the retractable door 120 and the ceiling 136 such that steam and heat may circulate into and out of the shower environment 102. The retractable door 120 may be formed of a flexible material (e.g., Mylar™, polyester, polyester, vinyl, canvas, cotton, etc.). The retractable door 120 may be treated with a water-replant coating on one side or both sides (e.g., wax, silicone, perfluorocarbons, etc.). The retractable door 120 may be resistant (e.g., impervious, etc.) to liquid water but may allow water vapor to permeate (e.g., pass through). In some embodiments, the retractable door 120 may be treated with an antimicrobial coating to prevent bacteria and mold from growing on the retractable door 120. The door cleaning assembly 302 may discharge a coating onto the retractable door 120 such that the coating is automatically re-applied to the retractable door 120. In some embodiments, the retractable door 120 must be re-coated or replaced regularly to maintain the desired amount of the coating.

The retractable door 120 includes a first door end 606 coupled to the spring roller 400 and a second door end 608 opposite the first door end 606. The second door end 608 is coupled to the handle portion 604. The handle portion 604 includes an elongate member (e.g., bar), shown as an edge guard 610. The edge guard 610 may be formed of plastic, metal, a metal alloy, or similar materials expressing inherent stiffness, resilience, and corrosion resistance. The edge guard 610 may be rigid enough such that the retractable door 120 is pulled taught (e.g., has no wrinkles, has a planar configuration) in an extended position and when transferring between the retracted position and an extended position. The edge guard 610 may define a length equal to the door height $L_H$ and be coupled to the entirety of the second door end 608. In some embodiments, the edge guard 610 includes a first guard end 612 that extends slightly above the retractable door 120 and a second guard end 614 that extends slightly below the retractable door 120 and slightly below the bottom wall 134. A distance between the first guard end 612 and the second guard end 614 is an edge guard length. The second guard end 614 may be positioned behind the shower step 500 such that the second guard end 614 prevents motion of the edge guard 610 and the retractable door 120 in front of the shower step 500 and away from the door plane $P_{door}$. In some embodiments, the edge guard 610 behaves as a guide that may selectively interface with the shower step 500 to provide haptic feedback to a user of the retractable door 120 as the user transitions the retractable door 120 between the retracted position and the extended position. Due to the flexibility of the retractable door 120, in some embodiments, the edge guard 610, and more specifically the second guard end 614, may not completely prevent a user from extending the retractable door 120 beyond the shower environment opening 108 and off of the door plane $P_{door}$. However, when a horizontal force is applied to the retractable door 120 via the handle portion 604 in a direction generally toward the first wall 130, the second door end 608 may interface with the rear step surface 504 to facilitate movement of the retractable door 120 along the door plane $P_{door}$.

When the retractable door 120 is in the retracted position, the edge guard 610 may interface with the housing 110 proximate to the door slot 404. The edge guard 610 may be structured such that the edge guard 610 is not pulled into the housing 110 by the force applied by the spring roller 400. In some embodiments, the edge guard 610 covers at least a portion of the door slot 404 when the retractable door 120 is in the retracted position. In some embodiments, the edge guard 610 covers the entirety of the door slot 404 when the retractable door 120 is in the retracted position.

The handle portion 604 also includes a grip 616 coupled to the edge guard 610 and configured to be interacted with by a user of the retractable shower door assembly 100 to transition the retractable door 120 between the first positon and the extended position. As shown in FIG. 7, the grip 616 extends away from the edge guard 610 is a direction generally toward the housing 110, the grip 616 corresponding to a first cut-out 618 within the retractable door 120 proximate to the second end 608. Generally speaking, the grip 616 is a member bent in a C- or U-configuration and coupled to the edge guard 610 to provide a handle (e.g., grip) for a user of the shower environment 102 to interact with to position the retractable door 120 between the retracted position and the extended position. A perimeter of the grip 616 sits flush with a perimeter of the first cut-out 618 when the edge guard 610 is coupled to the second door end 608. In some embodiments, the grip 616 is integrally formed with the edge guard 610.

The grip 616 and the first cut-out 618 may correspond to a second cut-out 620 defined by the housing 110 proximate to the door slot 404. When the retractable door 120 is in the retracted position, the grip 616 is positioned within the second cut-out 620. In some embodiments, the grip 616 is shaped such that the perimeter of the grip 616 sits flush against a perimeter of the second cut-out 620 when the retractable door 120 is in the retracted position. The second cut-out 620 may provide clearance to the grip 616 such that the edge guard 610 may sit flush against the housing 110 proximate to the door slot 404 and cover the entirely of the door slot 404.

Configured to be coupled to the first wall 130 (e.g., the second wall 132) is a latching member (e.g., closure member, coupling member, etc.) shown as a latch bar 622. The latch bar 622 is configured to retain the edge guard 610 proximate to the first wall 130 and maintain the retractable door 120 in the extended position. In other words, the latch bar 622 keeps the retractable door 120 extended across the shower environment opening 108. In still other words, the edge guard 610 is removably coupled (e.g., releasably coupled, selectively coupled, etc.) to the latch bar 622. The latch bar 622 may retain the edge guard 610 proximate to the first wall 130 using magnets, where the edge guard 610 is formed of a magnetic material. In some embodiments, where the spring roller 400 does not include an auto-lock and applies a force to the retractable door 120 in a direction toward the housing 110 when the retractable door 120 is in the extended position, the magnetic attraction (e.g., magnetic force) between the latch bar 622 and the edge guard 610 is greater than the force applied on the retractable door 120 by the spring roller 400. Generally speaking, a strictly horizontal force required to separate the edge guard 610 from the latch bar 622 when the edge guard 610 and latch bar 622 are coupled with one another is greater than the force applied on the retractable door 120 by the spring roller 400.

In some embodiments, the latch bar 622 includes clips or clasps configured to flex and mechanically hold the edge guard 610 proximate to the first wall 130. The latch bar 622 may include a projection that corresponds to a slot defined in the edge guard 610, such as a keyhole slot.

The latch bar 622 may be coupled to the first wall 130 along the door plane $P_{door}$. In some embodiments, the latch bar 622 is integrally formed with the first wall 130 (e.g., the first wall 130 is magnetized, the first wall 130 includes projections, etc.). In some embodiments, the latch bar 622 is positioned within a recess in the first wall 130 such that the edge guard 610 may sit flush against the first wall 130 when the latch bar 622 and the edge guard 610 are coupled together. The latch bar 622 defines a first latch end 624 and a second latch end 626 opposite the first latch end 624. The first latch end 624 and the second latch end 626 are separated by a latch length. In some embodiments, the latch length is equal to the edge guard length. In some embodiments, the latch length is less than the edge guard length. In some embodiments, the latch bar 622 defines a width approximately equal to a width of the edge guard 610 such that when the latch bar 622 is coupled to the edge guard 610, no portion of the latch bar 622 extends beyond the edges of the edge guard 610, protecting the latch bar 622 from the corrosive environment of the shower environment 102, and hiding the latch bar 622 from view when viewed from most angles.

While this specification contains many specific implementation details, these should not be construed as limitations on the scope of what may be claimed but rather as descriptions of features specific to particular implementations. Certain features described in this specification in the context of separate implementations can also be implemented in combination in a single implementation. Conversely, various features described in the context of a single implementation can also be implemented in multiple implementations separately or in any suitable subcombination. Moreover, although features may be described as acting in certain combinations and even initially claimed as such, one or more features from a claimed combination can, in some cases, be excised from the combination, and the claimed combination may be directed to a subcombination or variation of a subcombination.

As utilized herein, the term "approximately," "generally," and similar terms are intended to have a broad meaning in harmony with the common and accepted usage by those of ordinary skill in the art to which the subject matter of this disclosure pertains. It should be understood by those of skill in the art who review this disclosure that these terms are intended to allow a description of certain features described and claimed without restricting the scope of these features to the precise numerical ranges provided. Accordingly, these terms should be interpreted as indicating that insubstantial or inconsequential modifications or alterations of the subject matter described and claimed are considered to be within the scope of the present disclosure as recited in the appended claims.

The term "coupled" and the like, as used herein, mean the joining of two components directly or indirectly to one another. Such joining may be stationary (e.g., permanent) or moveable (e.g., removable or releasable). Such joining may be achieved with the two components or the two components and any additional intermediate components being integrally formed as a single unitary body with one another, with the two components, or with the two components and any additional intermediate components being attached to one another.

It is important to note that the construction and arrangement of the system shown in the various example implementations is illustrative only and not restrictive in character. All changes and modifications that come within the spirit and/or scope of the described implementations are desired to be protected. It should be understood that some features may not be necessary, and implementations lacking the various features may be contemplated as within the scope of the application, the scope being defined by the claims that follow. When the language "a portion" is used, the item can include a portion and/or the entire item unless specifically stated to the contrary.

Also, the term "or" is used in its inclusive sense (and not in its exclusive sense) so that when used, for example, to connect a list of elements, the term "or" means one, some, or all of the elements in the list. Conjunctive language such as the phrase "at least one of X, Y, and Z," unless specifically stated otherwise, is otherwise understood with the context as used in general to convey that an item, term, etc. may be either X, Y, Z, X and Y, X and Z, Y and Z, or X, Y, and Z (i.e., any combination of X, Y, and Z). Thus, such conjunctive language is not generally intended to imply that certain embodiments require at least one of X, at least one of Y, and at least one of Z to each be present, unless otherwise indicated.

Additionally, the use of ranges of values (e.g., W to P, etc.) herein are inclusive of their maximum values and minimum values (e.g., W to P includes W and includes P, etc.), unless otherwise indicated. Furthermore, a range of values (e.g., W to P, etc.) does not necessarily require the inclusion of intermediate values within the range of values (e.g., W to P can include only W and P, etc.), unless otherwise indicated.

What is claimed is:

1. A retractable shower door assembly comprising:
    a housing including a shelving cavity;
    a retractable door operable to move between a retracted position in which the retractable door is retracted into the housing and an extended position in which the retractable door extends out of the housing;
    a spring roller configured to bias the retractable door toward the housing when the retractable door is between the retracted position and the extended position; and
    a cleaning assembly positioned within the housing, the cleaning assembly comprising:
    a proximity sensor configured to sense at least one of a position of the retractable door or a movement of the retractable door, and
    an ultraviolet light source communicably coupled to the proximity sensor and is configured to direct ultraviolet light toward at least one surface of the retractable shower door based on the position of the retractable door or the movement of the retractable door.

2. The retractable shower door assembly of claim 1, further comprising an edge guard coupled to the retractable door opposite the spring roller, the edge guard configured to be removably coupled proximate to a wall opposite the housing.

3. The retractable shower door assembly of claim 2, wherein the edge guard further comprises a grip extending away from the edge guard and toward the housing.

4. The retractable shower door assembly of claim 1, further comprising a latch body configured to releasably couple an end of the retractable door opposite the spring roller proximate to a wall opposite the housing, the latch body configured to maintain the retractable door in the extended position.

5. The retractable shower door assembly of claim 1, wherein the cleaning assembly positioned within the housing and configured to apply a cleaning solution to the retractable door.

6. The retractable shower door assembly of claim 1, wherein the housing further comprises a shelf removably positioned within the shelving cavity.

7. The retractable shower door assembly of claim 1, further comprising a roller positioned within the housing end configured to facilitate a path of the retractable door as the retractable door transitions between the retracted position and the extended position to prevent the retractable door from interfacing with the housing.

8. The retractable shower door assembly of claim 1, further comprising a mounting body configured to couple the housing to a first wall, wherein the retractable door is configured to extend to a second wall opposite the first wall to cover an opening into a shower environment when the retractable door is extended.

9. The retractable shower door assembly of claim 8, wherein the housing includes a mounting cavity configured to surround the mounting body when the housing is coupled to the first wall so the housing can interface with the first wall.

10. A retractable shower door assembly comprising:
a housing comprising a shelving cavity extending into the housing and configured to removably receive a shelf within the shelving cavity;
a spring roller positioned within the housing and extending along a length of the housing;
a retractable door operably coupled to the spring roller and operable between a fully extended position and a retracted position, the retractable door comprising:
a first door end coupled to the spring roller; and
a second door end extendable away from the housing;
wherein the spring roller applies a unidirectional force to the retractable door to facilitate retraction of the retractable door into the housing; and
a cleaning assembly positioned within the housing, the cleaning assembly comprising a proximity sensor configured to sense at least one of a position of the retractable door or a movement of the retractable door and an ultraviolet light source configured to couple to the proximity sensor and is configured to direct ultraviolet light toward at least one surface of the retractable shower door based on the position of the retractable door or the movement of the retractable door.

11. The retractable shower door assembly of claim 10, wherein the spring roller comprises an auto-lock feature configured to selectively prevent the spring roller from retracting the retractable door.

12. The retractable shower door assembly of claim 10, further comprising:
an edge guard coupled to the second door end, the edge guard extending along the entirety of a height of the second door end; and
a grip extending away from the edge guard and toward the housing.

13. The retractable shower door assembly of claim 10, further comprising a latch body configured for coupling with a surface opposite to the housing when the housing is positioned within a shower environment, the latch body removably coupled with the second door end.

14. The retractable shower door assembly of claim 10, wherein the cleaning assembly positioned within the housing and configured to apply a cleaning solution to the retractable door.

15. A retractable shower door assembly comprising:
a housing comprising:
a first housing end and a second housing end;
a cavity between the first housing end and the second housing end; and
a door slot in fluid communication with the cavity, the door slot extending between the first housing end and the second housing end;
a spring roller positioned within the cavity between the first housing end and the second housing end;
a retractable door extending through the door slot, operably coupled to the spring roller, and positionable between a fully extended position and a retracted position; and
a cleaning assembly positioned within the housing, the cleaning assembly comprising:
a proximity sensor configured to sense at least one of a position of the retractable door or a movement of the retractable door, and
an ultraviolet light source communicably coupled to the proximity sensor and is configured to direct ultraviolet light toward at least one surface of the retractable shower door based on the position of the retractable door or the movement of the retractable door.

16. The retractable shower door assembly of claim 15, wherein the spring roller comprises an auto-lock feature configured to selectively prevent the spring roller from retracting the retractable door.

17. The retractable shower door assembly of claim 15, further comprising:
an edge guard coupled to the retractable door, the edge guard extending along the entirety of a height of the retractable door;
wherein the edge guard is structured to cover the door slot when the retractable door is in the retracted position.

18. The retractable shower door assembly of claim 15, wherein:
the housing further comprises a flange extending away from the second housing end; and
the door slot extends into the flange.

19. The retractable shower door assembly of claim 15, wherein the cleaning assembly is configured to apply at least one of a cleaning solution or ultraviolet light to the retractable door.

* * * * *